United States Patent [19]

Metz-Stavenhagen et al.

[11] Patent Number: 5,683,390
[45] Date of Patent: Nov. 4, 1997

[54] CORRECTING A SPINAL COLUMN

[75] Inventors: Peter Metz-Stavenhagen, Bad Wildungen; Bernd Robioneck, Schellhorn, both of Germany

[73] Assignee: Howmedica GmbH, Schoenkirchen, Germany

[21] Appl. No.: 391,862

[22] Filed: Feb. 22, 1995

[30]  Foreign Application Priority Data

Feb. 22, 1994 [DE]  Germany ............................ 9402839 U

[51] Int. Cl.⁶ ............................................. A61B 17/70
[52] U.S. Cl. ................................................ 606/61; 606/73
[58] Field of Search .......................... 606/59–61, 69, 606/72, 73, 80

[56]  References Cited

U.S. PATENT DOCUMENTS 4,887,596  12/1989  Sherman .
5,217,497  6/1993  Mehdian .
5,257,993  11/1993  Asher .
5,496,321  3/1996  Puno et al. ................................ 606/61

FOREIGN PATENT DOCUMENTS 2624720  6/1989  France .
4107480  9/1992  Germany .

*Primary Examiner*—Michael Buiz
*Assistant Examiner*—David O. Reip
*Attorney, Agent, or Firm*—Peter C. Richards; Lawrence C. Akers; Elizabeth O. Slade

[57]  ABSTRACT

An apparatus for correcting a spinal column having damaged vertebrae comprises a fastener (which is preferably a pedicle screw) having a receiving slot for holding a distracting or compressing bar. The bar is positioned within the slot in a manner permitting adjustment and is then locked in a fixed position, both functions achieved by a special two-part locking element which first holds and then rigidly locks the bar and fastener together. A method for correcting a spinal column having damaged vertebrae is also given.

14 Claims, 2 Drawing Sheets

5,683,390

CORRECTING A SPINAL COLUMN

BACKGROUND OF THE INVENTION

The present invention relates to an apparatus for correcting a spinal column having damaged vertebrae.

Supporting means for the human spinal column including coacting lamina hooks and pedicle screws are conventional. British patent 2 131 300 discloses a compressing apparatus, while U.S. Pat. No. 4,382,483 relates to a distracting apparatus. The bar bridges a number of vertebrae and does not permit properly affecting the vertebrae lying between the lamina hooks.

WO 91/01691 discloses an apparatus for lacing vertebrae of a spinal column in which pedicle screws having slotted heads are used and into which a bar is inserted. The legs of the slotted screw heads comprise an outer threaded portion, onto which a nut is screwed which abuts against the bar to fix it in position. EP 0 443 892 discloses a similar apparatus in which the slotted head of the pedicle screw includes an internal threaded portion receiving a solid screw which is brought into engagement with a fluted or, respectively, roughened bar to again fix the relative position of the bar and the individual pedicle screws. A ring surrounding the head of the pedicle screw prevents the legs of the screw head from pushing apart when the bar is fixed; otherwise the threaded engagement between the fixing screw and the pedicle screw head would be lost. A similar apparatus is shown in WO 90/09156.

Still further, G 92 02 745 discloses an apparatus of the type referred to above in which the pedicle screw is formed as a bipartite member, wherein the screw shaft includes a spherical end which is received in a ball-shaped recess which forms a receiving slot for the distracting or compressing bar. A fixing screw is screwed into an internal thread portion of the ball-shaped recess to urge the distracting bar onto the ball. G 93 02 700 further teaches providing a similar ball-shaped recess with an internal threaded portion onto which a head nut is screwed (which includes a central pin which can be brought into engagement with the distracting or compressing bar for fixing). The support between the ball-shaped recess and the hook or the pedicle screw (which is pivotal before the final fixing is completed) results in the advantage that the fastener on one hand and the ball-shaped recess on the other hand may be angularly oriented with respect to each other. Accordingly, the bar has to be bent to a less extent which is true for a sagital and lateral orientation.

As far as the devices just referred to provide for screwing the primary locking element shaped as a cap nut or as a screw is screwed on the locking element, the distracting or compressing bar is initially fixed and a distraction or compression may be performed in a manner known per se. Subsequently, the primary locking element is completely locked to produce a rigid connection between the locking element and the bar. The known devices require primary locking elements which must be screwed onto the locking element for a sufficient time in order to obtain a rigid initial fixing of the bar. The range of laterally moving the bar is thus not particularly large.

It is an object of the present invention to provide an apparatus for correcting a spinal column having damaged vertebrae in which after inserting a distracting or compressing bar, this bar may be initially secured so that it has sufficient play within the locking element, but can be rigidly secured later.

The object referred to is solved by the features of the invention.

SUMMARY OF THE INVENTION

According to the invention, the apparatus provides for a pair of locking elements, located at the free end of the fastener, wherein the primary locking element cooperates with a threaded portion of second locking element to rigidly secure the bar, which second locking element is fixed to the fastener in an appropriate manner.

A variety of different embodiments is conceivable to fix the second locking element to the free end of the fastener. According to the invention, an embodiment is provided according to which the second locking element is plate-like formed to be inserted into opposite grooves which are provided in the wall of the receiving slot. The grooves may be closed at one end to prevent the second element from falling out. The grooves may be wedge-shaped either alternatively or in addition to coact with the second plate-shaped locking element in a clamping relation. Inserting the plate-shaped second locking element is relatively simple which facilitates using the apparatus according to the invention for the surgeon.

According to a further alternative design the threaded portion of the second locking element is formed in the front face of a cap nut which may be screwed onto the outer thread portion of the anchoring element provided in the vicinity of the receiving slot.

BRIEF DESCRIPTION OF THE DRAWINGS

The invention is hereinafter described in more detail with reference to the drawings which show.

DESCRIPTION OF THE PREFERRED EMBODIMENTS

Figure 1:
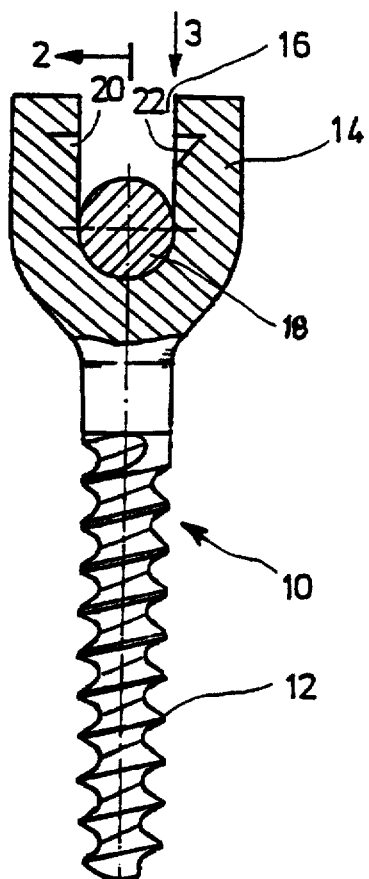
FIG. 1 is a sectional view of a pedicle screw including a distracting or compressing bar.
Figure 2:
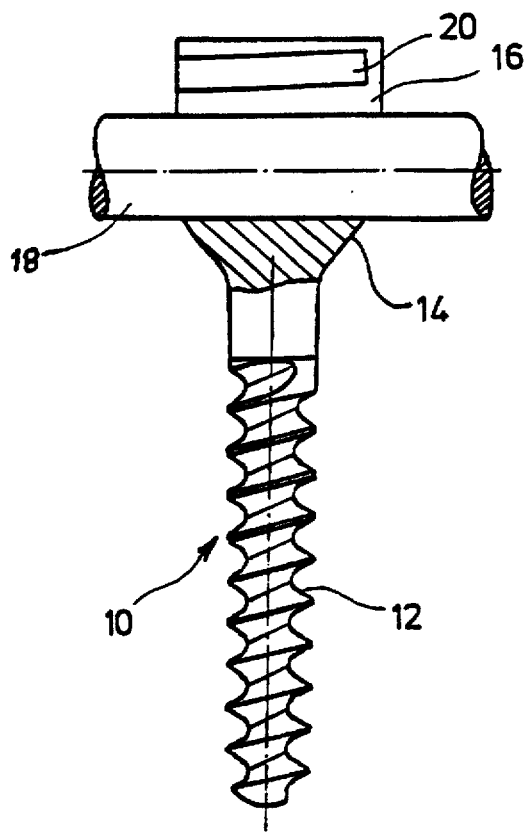
FIG. 2 is a sectional view of FIG. 1 along line 2—2.
Figure 3:
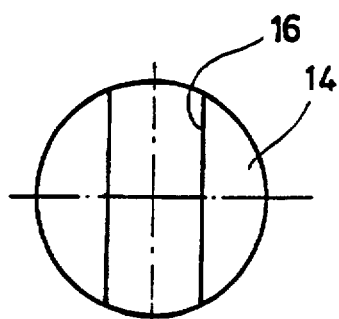
FIG. 3 is a top view of the pedicle screw of FIG. 1.

The pedicle screw 10 comprises a screw shaft 12 and a head 14, the outer periphery of which is substantially cylindrical and includes a central receiving slot 16 which is open towards the top end. The bottom of the slot has a cylindrical cross-section to closely fit a distracting or compressing bar 18. Above the bar 18 the side walls of the slot 16 are formed with grooves 20, 22 having a V-shaped cross-section. FIG. 1 shows that the upper side of the V-shaped groove is perpendicularly oriented with respect to the longitudinal axis of the slot. FIG. 2 shows that the grooves 20, 22 are closed at one end and include a slope with respect to the horizontal.

Figure 4:
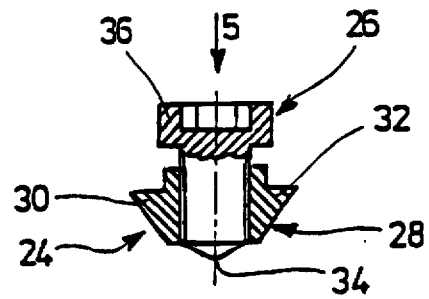
FIG. 4 is a sectional view of a locking element to be used with a pedicle screw according to FIGS. 1 and 2.
Figure 5:
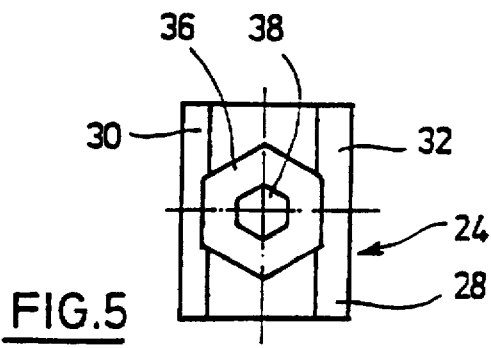
FIG. 5 is a top view of the locking element shown in FIG. 4 in the direction of arrow 5.

FIGS. 4 and 5 show a combination 24 of a first locking element 26 and a second locking element 28. The second locking element 28 includes a pair of faces 30, 32 being triangular in cross-section which are shaped to fit into the grooves 20, 22. However, there may be provided a slight clamping action in order to fix the plate 28 within the grooves 20, 22. The plate 28 has a central threaded portion for receiving the first locking element 26 which is defined by a fixing screw having a tip 34 at the end of the shaft and an opposite head 36 which is provided with an external as well as an internal hexagonal configuration 38. When the combination 24 is inserted into the grooves 20, 22 after the bar 18 has been inserted in the slot 16, the bar has sufficient play, but is secured from being moved out of the slot 16. After completing the distraction or compression, the screw 26 is actuated until the tip 34 firmly contacts the bar 18 to complete locking the bar to the head of the pedicle screw 10.

As mentioned before, the plate 28 is inserted into the grooves 20, 22 from one side thereof. However, a plate may be conceived which is placed from above into the slot 16, wherein its length side is oriented toward the length side of the slot 16. Subsequently, the plate is turned about some 90° so that the sides thereof enter the grooves 20, 22. It should be understood that other than V-shaped groove shapes may be provided.

Figure 6:
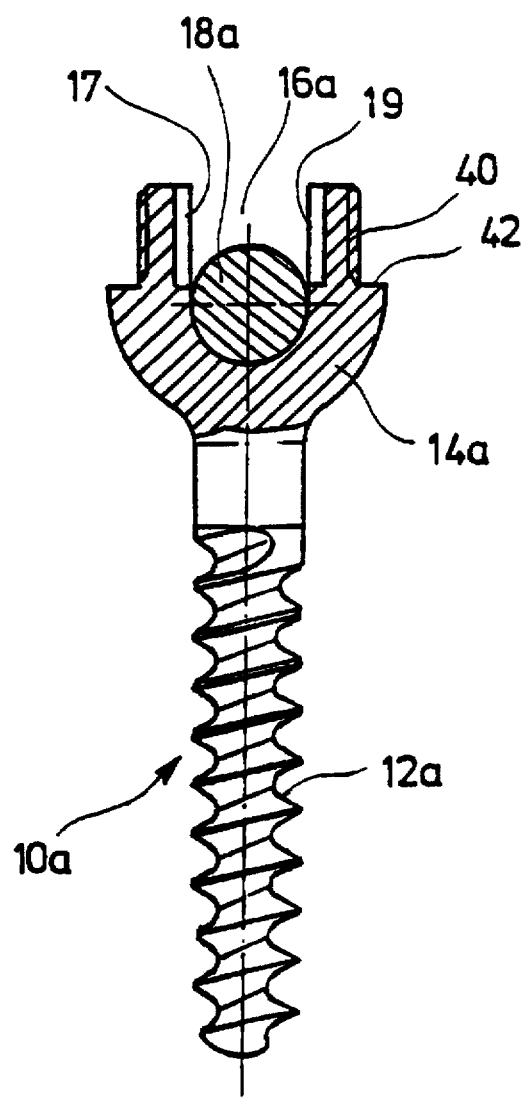
FIG. 6 is a sectional view of a further embodiment of a pedicle screw and a compressing or distracting bar.

The pedicle screw 10a shown in FIG. 6 comprises a threaded shaft 12a and a head 14a having a lower side which is shaped similar to the head 14 of the pedicle screw shown in FIGS. 1 and 2. The head also includes a receiving slot 16a for inserting a distracting or compressing bar 18a. The walls of the slot 16a are provided with opposite ribs 17, 19 which are substantially located centrally with respect to the slot 16a. The head 14a has an upper portion including an outer thread 40 ending at a shoulder 42. A cap nut 46 comprises an inner thread 44 which is screwed on the outer thread 40. The cap nut 46 includes a threaded portion provided in the front wall 48 to receive a fixing screw 50 having a hexagonal head 52 including an internal hexagonal configuration 54. At the side opposite the threaded portion 44 there is an axial flange 56 integrally formed to the front wall 48 accomodating the head 52 of the screw 50 when being screwed in.

Figure 7:
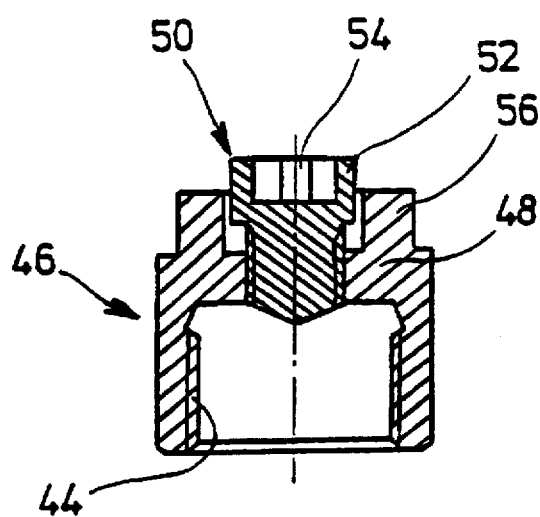
FIG. 7 is a combination of a pair of locking elements for the pedicle screw of FIG. 6.

In screwing the cap nut 46 onto the head 14a of the pedicle screw 10a, the distracting or compressing bar 18a is initianally fixed and can move in an axial direction as well as perpendicularly thereto. By fixing the screw 50, the bar 18a is then finally secured to the pedicle screw 10a. In the embodiment of FIGS. 6 and 7 the final fixing may be performed by the nut 46 becoming seated on the bar as well as by means of the fixing screw 50.

It should be understood that lamina hooks, for example may be provided as anchoring means instead of the pedicle screws, which hooks are then provided with a head similar to that of the pedicle screws shown. It should be further understood that the shanks of the pedicle screws may be separate with respect to the heads which can be shaped to define ball-shaped recesses for receiving balls formed at the upper end of the screw shanks. This similarly applies for lamina hooks having a ball.

What is claimed is:

1. An apparatus for correcting a spinal column having damaged vertebrae comprising (a) a fastener to be secured to one of two adjacent vertebrae, said fastener comprising a pedicle screw and including a threaded shaft portion and a free end, which fastener has an axis and a receiving slot at said free end to receive a distracting or compressing bar, said receiving slot having walls within which are provided oppositely disposed V-shaped grooves (20,22), and (b) a first locking element including a threaded portion which may be secured onto the bar disposed in said receiving slot and (c) a second locking element (28) which can be fixed to said free end of said fastener (10,10a) and which threadably receives said first locking element (26), and wherein said second locking element (28) has a planar bottom portion and tapering side portions which taper uniformly with respect to said axis of said pedicle screw, wherein said tapering side portions have ends which are V-shaped in cross-section and which mate with said oppositely disposed V-shaped grooves (20,22).

2. Apparatus of claim 1 wherein the grooves (20,22) are closed at one end thereof.

3. Apparatus of claim 2, wherein the grooves (20,22) are sloped with respect to the horizontal.

4. Apparatus of claim 3, wherein said second locking element (28) is received in said grooves (20,22) in a clamping manner.

5. Apparatus of claim 1, wherein said grooves (20,22) have a V-shaped cross-section and wherein one side thereof is defined by the groove wall.

6. Apparatus of claim 5, wherein the side of the groove wall facing away from the anchoring means (12) extends perpendicular with respect to the longitudinal axis of the slot (16).

7. An apparatus for correcting a spinal column having damaged vertebrae comprising:

(a) a fastener to be secured to a vertebra, said fastener having a free end, having a shaft portion, and having a receiving slot located near said free end to receive a bar, said receiving slot having walls in which are provided oppositely disposed grooves, (b) a first locking element including a first threaded portion which can be secured onto said bar which is disposed in said receiving slot, and (c) a second locking element which can be fixed to said free end of said fastener and which threadably receives said first locking element by means of a second threaded portion and wherein said second locking element (28) has a planar bottom portion and tapering side portions which taper uniformly with respect to said axis of said pedicle screw, wherein said tapering side portions have ends which are V-shaped in cross-section and which mate with said oppositely disposed V-shaped grooves (20,22).

8. Apparatus of claim 7, wherein each of said grooves is closed at one end thereof.

9. Apparatus of claim 8, wherein said grooves are sloped with respect to the horizontal.

10. Apparatus of claim 9, wherein said second locking element is received in said grooves in a clamping manner.

11. Apparatus of claim 9, wherein said grooves have a V-shaped cross-section and wherein a first side of said V-shaped cross-section is defined by a wall of said groove.

12. Apparatus of claim 11, wherein said perceiving slot has a longitudinal and wherein said first side of said V-shaped cross-section is located facing away from said shaft and extends perpendicular with respect to said longitudinal axis of said slot.

13. A method for correcting a spinal column having damaged vertebrae comprising:

(a) securing to a vertebra a fastener comprising a shaft portion having an axis, a free end, and a receiving slot located near said free end for receiving a bar and having oppositely disposed V-shaped grooves located within walls of said slot, (b) inserting said bar into said slot and fixing said bar in said receiving slot by means of a first locking element including a first threaded portion, and (c) rigidly fixing said bar in said free end of said fastener by means of a second locking element which threadably receives said first locking element, said second locking element having a planar bottom portion and tapering side portions which taper uniformly with respect to said axis of said fastener, wherein said tapering side portions have ends which are V-shaped in cross-section and which mate with said oppositely disposed V-shaped grooves (20,22).

14. A method according to claim 13, wherein each of said grooves is closed at one end thereof, wherein said grooves are inclined with respect to the horizontal, and wherein said grooves have a V-shaped cross-section.

* * * * *